US00PP23422P2

(12) United States Plant Patent
Ramming et al.

(10) Patent No.: US PP23,422 P2
(45) Date of Patent: Feb. 26, 2013

(54) GRAPEVINE DENOMINATED 'VALLEY PEARL'

(50) Latin Name: *Vitis vinifera L.*
Varietal Denomination: Valley Pearl

(75) Inventors: David Ramming, Fresno, CA (US); Ronald E. Tarailo, Fresno, CA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 13/199,300

(22) Filed: Aug. 25, 2011

(51) Int. Cl.
*A01H 5/00* (2006.01)

(52) U.S. Cl. ..... Plt./207

(58) Field of Classification Search ..... Plt./207
See application file for complete search history.

(56) References Cited

U.S. PATENT DOCUMENTS

PP1,250 P 7/1953 Fujihara
PP4,329 P 10/1978 Kitahara
PP4,873 P 8/1982 Corrin
PP5,047 P 5/1983 Garabedian
PP5,151 P 12/1983 Hahn et al.
PP5,908 P 3/1987 Garabedian
PP5,987 P 5/1987 Garabedian
PP6,295 P 9/1988 Tzori
PP8,297 P 7/1993 Olmo
PP8,298 P 7/1993 Newby, Jr. et al.
PP10,434 P 6/1998 Cain
PP11,012 P 7/1999 Reisch et al.
PP11,727 P 12/2000 Cain
PP11,820 P2 3/2001 Cain
PP12,189 P2 11/2001 Karniel
PP12,696 P2 6/2002 Karniel
PP14,193 P2 9/2003 Otani
PP14,773 P2 5/2004 Bourne
PP14,923 P3 6/2004 Bourne
PP15,110 P2 8/2004 Cain et al.
PP16,177 P3 1/2006 Cain et al.
PP16,284 P2 2/2006 Ramming et al.
PP16,399 P3 4/2006 Ellis et al.
PP17,504 P3 3/2007 Maranto

*Primary Examiner* — Annette Para
(74) *Attorney, Agent, or Firm* — Gail E. Poulos; John D. Fado; Lesley Shaw

(57) ABSTRACT

A new and distinct variety of grapevine denominated 'Valley Pearl' which is characterized by its early to mid-season ripening seedless fruit, attractive green coloration, its round fruit shape, its firm fruit texture with neutral sweet flavor, and its high production when spur pruned.

2 Drawing Sheets

Latin name of the genus and species of the plant claimed: 'Valley Pearl' is a new grapevine plant that is *Vitis vinifera* L.

Variety denomination: The new grapevine plant claimed is of the variety denominated 'Valley Pearl'.

BACKGROUND OF THE INVENTION

The present invention relates to a new and distinct variety of grapevine, *Vitis vinifera* L., which will hereinafter be denominated varietally as the 'Valley Pearl' grapevine, and, more particularly, to a grapevine which has fruit maturing for commercial harvesting and shipment approximately July 25 in the San Joaquin Valley of central California. The fruit has attractive white skin coloration at maturity with round shape and seedless berries.

The grapevine of the present invention originated from a hand-pollinated cross of 'A60-42' (unpatented) and 'C77-79' (unpatented) made in 1996 in Fresno Calif. The female was 'A60-42', a seedless, white-fruited grapevine with reflex anthers in the flower, round berries with firm flesh and good skin, and slight muscat flavor. The fruit of the 'A60-42' ripen about four weeks after the instant variety. The pollen parent was 'C77-79' a seedless, white fruited grape with medium size, round to ovate berries with medium skin and medium firm flesh. The fruit of the 'C77-79' grapevine ripen two weeks after the variety of the subject invention. Both of the parents of the instant cultivar are hybrids of the grapevine genus and species *Vitis vinifera* L.

The 494 aborted seeds resulting from this controlled hybridization were developed further through in vitro tissue culture and germinated in the laboratory during the fall of 1996. The resulting seedling population totaled 37 individual plants. All seedlings were planted in the spring of 1997 in a vineyard at in Fresno, Calif. The seedlings fruited in the summer of 1999 and one, the grapevine of the present invention, was designated as 'A85-40' and selected for its attractive early ripening, very large, white seedless berries, and good fruit quality.

In 2000, the grapevine of the subject invention was propagated asexually by rooting hardwood cuttings at Fresno, Calif. and a test planting of two grapevines of the subject invention was established in Fresno, Calif. Subsequently in 2001 a larger test planting of 24 vines was established with rooted hardwood cuttings of the instant invention. The instant cultivar rooted readily from hardwood cuttings. All grapevines of the new variety planted from hardwood cutting propagation, fruited in the third season of growth after planting. All propagules, or resulting plants, of the present invention have been observed to be true to type in that all asexual reproduced grapevines of the variety possessed the characteristics identical to those of the originally discovered grapevine.

SUMMARY OF THE INVENTION

The grapevines of the subject invention possess medium vigor and have produced fruit as own-rooted grapevines. The size of the grapevines was determined by growing the grapevines on a three cross arm 'T' type trellis structure with a top cross arm of approximately 122 cm in length set approximately 188 cm above the ground; a second cross arm of approximately 107 cm in length set approximately 152 cm above the ground; and a third cross arm approximately 91 cm in length set approximately 117 cm above the ground. The trellis structure had two wires per cross arm and indicted a grapevine height of approximately 236 cm and a grapevine spread of approximately 175 cm.

The fruit of the new variety ripens early to mid-season, about the same time as the 'Sugraone' grapevine (U.S. Plant Pat. No. 3,106). The average ripening date in Fresno, Calif. is July 25. Berries adhere very well to the fruit pedicel and have minimal shatter from the clusters during storage. The fruit is attractive green in color at maturity. The fruit shape is round. Fruit skins are similar in thickness to 'Perlette' (non-patented) grapevine and 'Sugraone' grapevine (U.S. Plant Pat. No. 3,106). The pulp of the fruit adheres to the skins of the berry and the fruit texture is firm and meaty. The berries are medium to large in size, or approximately 7.2 grams. The flavor of the fruit is sweet and has been rated high. Soluble solids concentration of the juice at fruit maturity averages approximately 17.4% with titratable acid of approximately 0.48 grams/100 milliliters of juice. The fruit is of the stenospermocarpic type of seedlessness and contains small, aborted seed traces that are not noticeable when eaten. The fruit clusters are usually borne on the average of 1.3 per shoot on spur pruned vines. The fruit clusters are conical and are large in size, or approximately 1,112 grams, medium to tight density and attractive. The fruit cluster peduncles are thick and medium in length. The grapevine and fruit of the new variety are susceptible to powdery mildew disease of grape plants. A spray program for powdery mildew disease control is required.

BRIEF DESCRIPTION OF THE DRAWINGS

The drawings of the grapevine of the present invention are color photographs showing in FIG. 1 a typical specimen of the fruit and in FIG. 2 a shoot with leaves and a flower cluster all of the new variety of the present invention.

The color of the photographs is as nearly true as it is reasonably possible to provide in such color photographs. Description of the new invention applies to vines of 'Valley Pearl' grown on its own roots at a density of 1,119 vines per hectare in Fresno County, Calif. in 2004/2005. These vines were in their second/third year of full production having been planted in 2001.

DETAILED BOTANICAL DESCRIPTION

Figure 1:
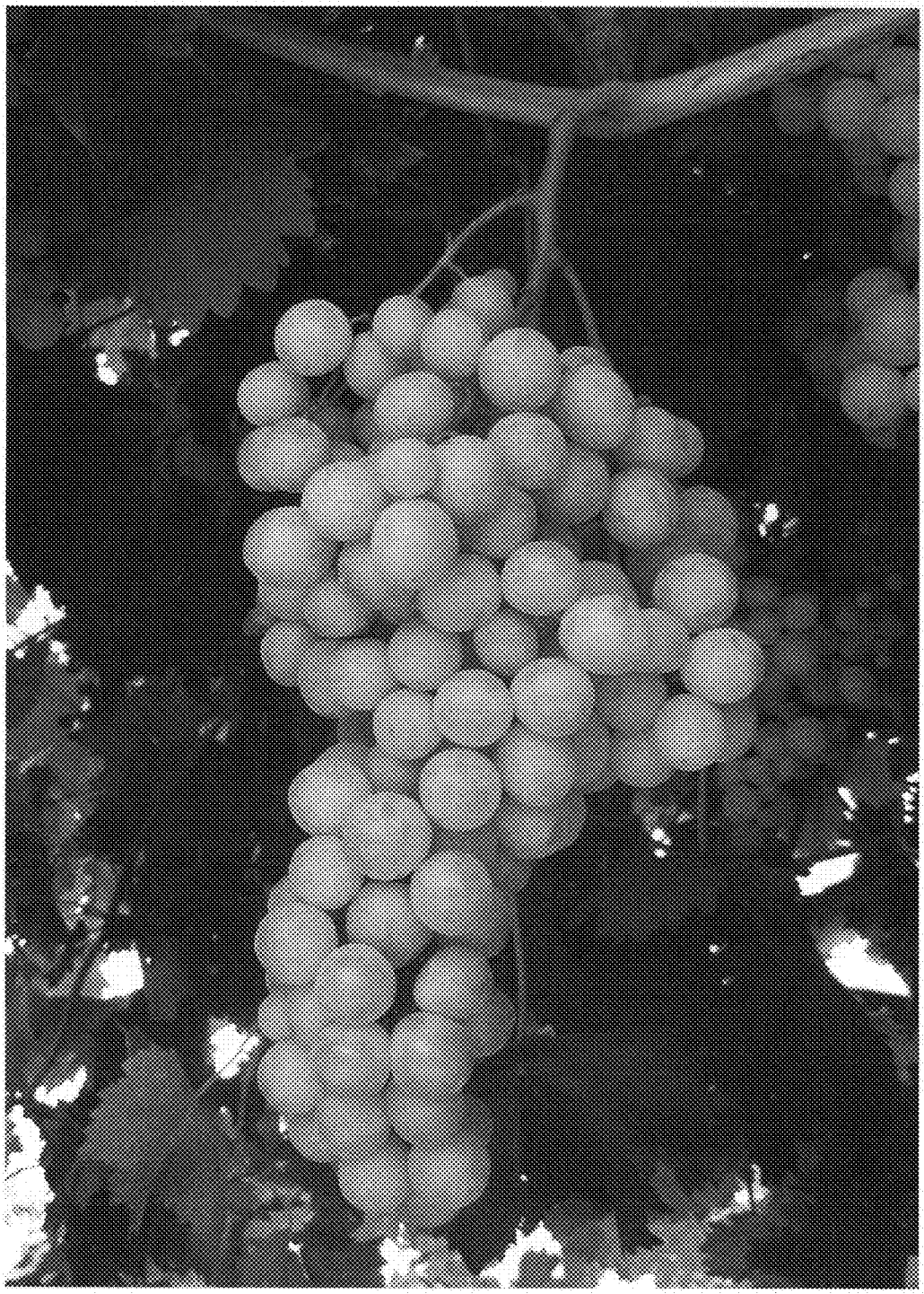
Figure 2:
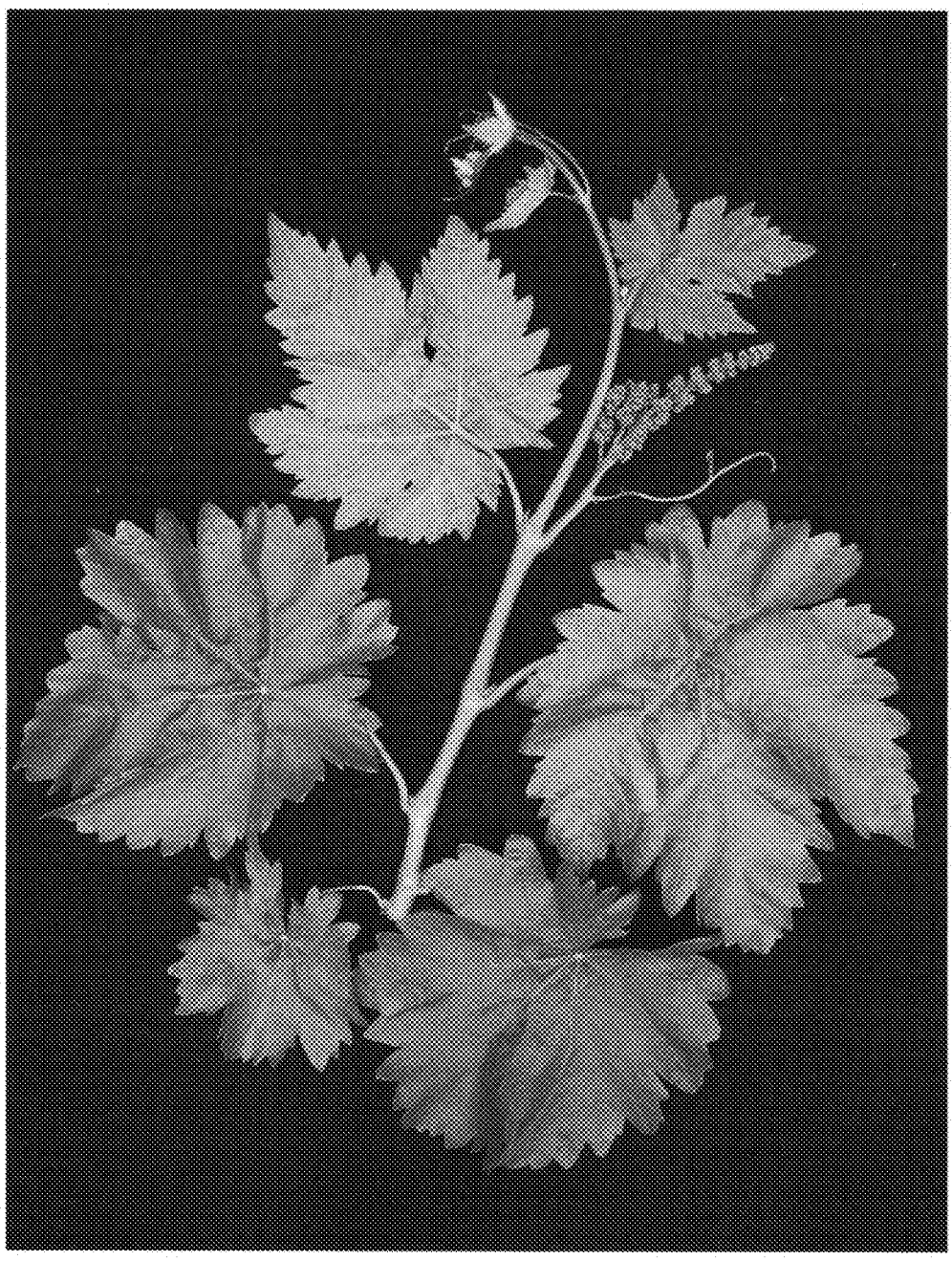

The following is a detailed description of the botanical and pomological characteristics of the subject grape vine. All major color code designations are by reference to the *Dictionary of Color*, by Maerz and Paul, First Edition, 1930.

The new variety cv. 'Valley Pearl' may be distinguished from other commercial grape cultivars known to us by a combination of characteristics, including its early to mid-season ripening seedless fruit with attractive green coloration, its firm and meaty fruit texture with a neutral sweet flavor, its round fruit shape, large berry size and its medium to tight density cluster.

The new variety of grapevine is most similar to its mother parent 'A60-42' by having white skin coloration and firm fruit texture. It is distinguished therefrom and an improvement thereon in a number of fruit characteristics. The berry size is larger, and the aborted seed is smaller. The fruit ripens 4 weeks before 'A60-42'. The new variety has perfect flowers with functional male and female parts while 'A60-42' has only functional female parts. The new grapevine is also similar to the commercial variety 'Sugraone' (U.S. Plant Pat. No. 3,106) in that they ripen at the same time and have white seedless berries. It is distinguished therefrom and an improvement thereon in that the vines are productive on spurs, while 'Sugraone' needs to be pruned to canes to be commercially productive. It is also similar to the commercial variety 'Thompson Seedless' (unpatented), in that they have firm white seedless fruit. It is distinguished therefrom and an improvement thereon in that the berries of the new variety are larger, round and ripen earlier than does 'Thompson Seedless'.

The new variety also differs substantially from its male parent 'C77-79'. The most distinguishing difference is the thicker skin and firmer berries that ripen two weeks ahead of 'C77-79'.

Referring more specifically to the botanical details of this new and distinct variety of grapevine, the following has been observed under the ecological conditions prevailing at the orchard of origin which is located in Fresno in the San Joaquin Valley of central California. All major color code designations are by reference to the *Dictionary of Color*, by Maerz and Paul, First Edition, 1930. Common color names are also occasionally employed. Where dimensions, sizes, colors and other characteristics are given, it is to be understood that such characteristics are approximations of averages set forth as accurately as practicable. The description hereof was taken from specimens grown in Fresno, Calif. The grapevines used for measurement were grown in a fine sandy loam soil and the grapevines were irrigated using trickle, or drip irrigation. In a substantial part, the data hereof was from grapevines that were four to five (4-5) years old.

Vine:

*Size*.—Medium. Grapevine size as determined on grapevines growing on a three cross arm 'T' trellis with the top cross arm approximately 122 cm long set approximatley 188 cm above the ground; the second cross arm approximately 107 cm long set approximately 152 cm above the ground; and the third cross arm approximately 91 cm long set approximately 117 cm above the ground. There were two wires per cross arm and was trained to produce a grapevine height of approximately 236 cm and a grapevine spread of approximately 175 cm.

*Vigor*.—Medium vigor. Vigor as measured by weighing prunings at dormant pruning for spur pruned grapevines (with approximately 27 spurs and approximately 2 buds per spur) was approximately 8.78 Kg. Productivity — Productive, approximately 31.2 Kg per grapevine on grapevines spaced approximately 8 ft. (243.84 cm) by approximately 12 ft. (365.76 cm).

*Regularity of bearing*.—Regular. Annual pruning is required for reliable production.

Canes:

*Size*.—Diameter — Mature Canes — Medium diameter, medium vigor, upright in growth habit.

*Mature canes*.—Diameter — Internode Base — approximately 10.9 mm.

*Mature canes*.—Diameter — Internode Midpoint — approximately 10.3 mm.

*Mature canes*.—Diameter — Internode Tip — approximately 7.2 mm.

*Mature canes*.—Diameter — Node Base — approximately 13.6 mm.

*Mature canes*.—Diameter — Node Midpoint — approximately 12.3 mm.

*Mature canes*.—Diameter — Node Tip — approximately 9.9 mm.

*Internode length*.—Base — approximately 14.0 cm.

*Internode length*.—Midpoint — approximately 14.7 cm.

*Internode length*.—Tip — approximately 12.0 cm.

*Average length of canes*.—Approximately 388 cm.

*Surface texture*.—Smooth.

*Color of mature cane*.—Orange brown (plate 11 I6). No anthocyanin observed on mature canes.

Buds:

*Bud color*.—Brown (plate 15 H7).

*Bud texture*.—Smooth.

*Dormant bud* (*compound bud or eye*).—Width — At base of cane approximately 5.1 mm; at midpoint of cane approximately 5.1 mm and at tip of cane approximately 5.5 mm. The average number of buds on a current, single-season growth cane is approximately 36.

*Date of bud break*.—February 26, early season.

Shoots:

*Young shoots*.—Young shoots have white felty indument on leaves but stem and petiole are glabrous.

*Diameter of young shoots in spring*.—(Measured when shoots are approximately 12-24 inches). At base approximately 7.8 mm, at midpoint approximately 5.9 mm and at tip approximately 3.1 mm.

*Internode length*.—Approximately 6.4 cm at $4^{th}$ internode from base.

*Young shoots*.—Color — Pale green (plate 21 L7) with very slight red on edge.

*Interstem of shoot tip*.—Color — Green (plate 20 L7) with no red streaks on the sun exposed side.

*Shoot shape*.—Straight to slightly curved.

*Shoot tip*.—Form — Open.

Tendrils:

*Tendrils size*.—Length — approximately 21.3 cm.

*Tendrils size*.—Diameter — approximately 1.65 mm.

*Tendrils shape*.—Usually triforcated and curled on distal end.

*Tendrils pattern*.—Found beginning opposite node 6 and 7, then again at nodes 9, 10, 12, 13, 15, 16 with this repeating intermittent pattern to the distal end of the cane.

*Tendril color immature growth*.—Green (plate 20 L6) with red (plate 6 I2) only on youngest tendrils.

Leaves:

*Size*.—Leaves simple and alternate. The mid vein (L1) is approximately 14.6 cm long, vein L2 is approximately 12.6 cm long and vein L3 is approximately 9.4 cm long. The angle between the mid vein L1 and L3 is approximately 118 degrees and between L1 and the 1st vein off L3 is approximately 153 degrees.

*Average length*.—Approximately 21.9 cm.

*Average width*.—Approximately 21.7 cm.

*Shape*.—Orbicular.

*Lobe number*.—Approximately Five (5).

*Color*.—Upwardly Disposed Surface — Dark green (plate 23 L10). Upward surface is glabrous, undulate and smooth to slightly bullate.

*Color*.—Downwardly Disposed Surface — Green (plate 23 H8). Lower surface is glabrous with few short erect hairs at the junction of the main midrib vein with branching veins.

*Leaf vein*.—Color — Light green (plate 19 I4) with no red pigment on veins of leaf.

*Leaf vein*.—Thickness — Thickness of mid vein at center of leaf is approximately 1.5 mm.

*Leaf margin*.—Serrated with shape of teeth both sides convex and medium in size.

*Petiole sinus*.—Lyre shape and usually petiole lobes are strongly overlapped. On mature leaf is approximately 5.2 cm deep and approximately 1.1 cm wide at widest point.

*Petiole size*.—Medium.

*Petiole length*.—Approximately 13.5 cm.

*Petiole diameter*.—Approximately 4.2 mm.

*Petiole color*.—Green (plate 19 J3) with very slight red covering in sun.

*Young leaf*.—Color — Upper Surface — Green (plate 20 L8) with cobwebby indument on upper surface.

*Young leaf*.—Color — Lower Surface — Green (plate 20 L7) with cobwebby to downey indument on lower surface.

*Young leaf*.—Shape unfolded — Concave.

*Petiole of young leaf*.—Color — Green (plate 21 L6).

*Stipules*.—Small and onion skin.

Trunk:

*Size*.—Medium.

*Size*.—Height — Approximately 91 cm above the vineyard floor.

*Size*.—Diameter — Approximately 6.1 cm as measured just below the cordon or head point at approximately 71.1 cm above vineyard floor; and approximately 6.8 cm at approximately 15.2 cm above the vineyard floor.

*Bark*.—Color — dark brown (plate 8 C2).

Flowers:

*Flower size*.—Medium.

*Flower unopened*.—Diameter — approximately 0.7 mm.

*Flower unopened*.—Length — approximately 3.8 mm.

*Flower unopened*.—Surface Texture — Smooth.

*Date of bloom*.—First bloom about Apr. 27, 2005.

*Date of full bloom*.—About May 13, 2005 at 75%.

*Inflorescence*.—Panicle.

*Cluster size*.—At Bloom — Generally, medium.

*Cluster length*.—Approximately 20.6 cm.

*Cluster width*.—Approximately 30.7 cm.

*Peduncle length*.—Approximately 4.5 cm.

*Shape of cluster*.—Conical with well developed shoulders.

*Calyptra color*.—Green (plate 21 L9).

*Stamens*.—Five (5) and erect.

*Pistil*.—Well developed.

*Ovary color*.—Green (plate 22 K10).

*Pollen*.—Normal, fertile, abundant.

*Anthers*.—Color — Light yellow (plate 9 I1).

Fruit:

*Maturity when described*.—Ripe for commercial harvesting and shipment approximately third week of July in Fresno.

*Cluster size*.—Spur Pruned Vines — approximately 1,112 grams.
*Cluster length*.—Approximately 22.6 cm.
*Cluster width*.—Approximately 19.1 cm.
*Cluster shape*.—Conical.
*Cluster density*.—Medium, on average has approximately 155 berries per cluster.
*Clusters per vine*.—Approximately 124, spur pruned.
*Clusters per shoot*.—Approximately 1.3 clusters per shoot.

Peduncle:
*Size*.—Length — Medium, approximately 5.4 cm.
*Size*.—Diameter — Medium, approximately 5.8 mm.
*Color*.—Green (plate 21 L6).
*Texture*.—Smooth, glabrous.

Pedicel: There is good attachment between the berry and the pedicel.
*Size*.—Length — approximately 7.4 mm.
*Size*.—Diameter — approximately 3.2 mm.
*Color*.—Green (plate 20 K7).
*Texture*.—Glabrous with a few brown lenticels.
*Brush*.—Length — approximately 3.8 mm.
*Brush color*.—Light yellow green (plate 20 H1).

Berry:
*Size*.—Medium, avg. approximately 7.2 grams.
*Shape*.—Round.
*Length*.—Approximately 2.59 cm.
*Width*.—Approximately 2.25 cm.
*Color*.—Light green (plate 20 L1).
*Bloom*.—Medium.

Skin: Skin adheres to the flesh.
*Thickness*.—Medium in thickness.
*Texture*.—Smooth.
*Tendency to crack*.—None.

Flesh:
*Flesh color*.—Translucent and very light green (plate 20 K2).
*Texture*.—Firm, meaty.
*Juice production*.—Medium.
*Color of juice*.—Clear.
*Flavor*.—Sweet and neutral flavor. Slight muscat flavor in very ripe fruit exposed to light.
*Soluble solids*.—Approximately 17.4%.
*Titratable acid*.—Approximately 0.48 g/100 ml juice.
*Aroma*.—None.
*Ripening*.—Uniform.
*Eating quality*.—Good, sweet.

Disease resistance: Susceptible to powdery mildew, and fungicides were applied to the grapevines under evaluation to control powdery mildew.

Insect resistance: Insecticides were applied to the grapevines under evaluation to control grapevine leafhoppers and variegated leafhoppers. No resistances to these pests were determined in these evaluations due to chemical control of these pests.

Character of seeds: Stenospermocarpic seedless, averaging 3.1 small aborted seed traces per berry that are not noticeable when eaten. Average aborted seed trace size when present are 7.3 mg fresh weight, 3.7 mm long and 1.98 mm wide. Seed color is green (plate 21 K7).

Use: Fresh market. No wine nor raisin evaluations have been done.

Keeping quality: Very good.

Shipping and handling qualities: Berries ship and handle similar to 'Sugraone' and there is very little berry shatter.

Although the new variety of grapevine possesses the described characteristics noted above as a result of the growing conditions prevailing in Fresno, Calif. in the central San Joaquin Valley of California, United States of America, it is to be understood that variations of the usual magnitude and characteristics incident to changes in growing conditions, training, irrigation, fertilization, pruning, pest control, climatic variation and the like are to be expected.

We claim:

1. A new and distinct variety of grapevine substantially as illustrated and described, characterized by its attractive green color, round fruit shape, and firm flesh texture with a neutral sweet flavor and high production when spur pruned.

* * * * *